United States Patent [19]
Laux et al.

[11] Patent Number: 6,023,333
[45] Date of Patent: Feb. 8, 2000

[54] DEVICE AND METHOD FOR OPTICAL DETECTION OF THE DEFORMATION OF A SURFACE

[75] Inventors: Wolfram Laux, GroBhansdorf; Jurgen Klicker, Hoisdorf, both of Germany

[73] Assignee: Basler AG, Germany

[21] Appl. No.: 09/119,801

[22] Filed: Jul. 21, 1998

[30] Foreign Application Priority Data

Jul. 23, 1997 [DE] Germany .............. 197 31 545

[51] Int. Cl.$^7$ ............................................. G01B 11/30
[52] U.S. Cl. ............................. 356/371; 356/237.2
[58] Field of Search .............................. 356/237.2, 371, 356/367, 369

[56] References Cited

U.S. PATENT DOCUMENTS

4,948,258  8/1990  Caimi ............................ 356/376
5,477,332  12/1995 Stone et al. .................... 356/371
5,729,520  3/1998  Klicker .
5,757,978  5/1998  Flick et al. .................... 356/367

Primary Examiner—Richard A. Rosenberger
Attorney, Agent, or Firm—Howson and Howson

[57] ABSTRACT

Device for optical detection of the deformation of a surface with at least one photosensitive receiver having a matrix image plane, which is exposed by at least one light source. It is proposed according to the invention that the light source is constructed as a nearly point-source light with uncollimated light and in imaging optics are provided and adjusted such that the light source is imaged sharply onto the image plane (14) of the photosensitive receiver, so that the surface to be examined acts as a reflective surface, the light source having a known nominal position on the image plane in case of a flawless surface being examined, so that the deformation can be determined from the deviation of the actual position of the image of the light source from the known nominal position of the image of the light source on the image plane. With this arrangement, a deformation, in particular, an erroneous inclination of a CD or DVD, can be detected with high precision and by simple means.

33 Claims, 5 Drawing Sheets

DEVICE AND METHOD FOR OPTICAL DETECTION OF THE DEFORMATION OF A SURFACE

The invention pertains to a device and a method for optical detection of the deformation of a surface, with at least one receiver having a matrix image plane, which is illuminated by a light source. The invention pertains in particular to a device and a method for optical detection of the deformation of an essentially flat surface, such as the data side of a CD, DVD or corresponding optical data medium. The discussion therefore primarily speaks of a CD or DVD, without any restriction being connected therewith. Deformations are to be understood below to mean, among other things, tilting of a surface, in which a surface or a surface section is tilted, originating from a normal position of the surface.

It is frequently necessary to detect a possible erroneous deformation of a surface. Deformations can be shaped, for instance, as a warp [unconfirmed translation] or as surface sections tilted with respect to the flat surface. In optical data media such deformations have a particularly disadvantageous effect since, corresponding to the deformation, the optical scanning beam, a laser beam as a rule, experiences an undesired influence. This can lead to problems particularly for those CDs or DVDs which serve as pure data storage for data processing systems, since stored data can no longer be correctly retrieved and stored.

Devices are known in which the data side of a CD is irradiated by a point-source light beam from a laser. The beam reflected from the surface or mirror layer of the CD is directed onto a position-sensitive detector, a four-quadrant diode, for instance. In case of an impermissible deflection, one of the quadrants is illuminated, so that a fault can be recognized. In this measuring method, the CD is ordinarily rotated by 360°, so that a deformation can be detected only along a radius.

Such a measurement along only one radius will as a rule no longer be sufficient, since requirements for surface accuracy continue to increase due to the ever-increasing data density. Thus, according to the newest requirements applying to DVDs, the scanning beam may be deflected by only 0.8° radially and by only 0.3° tangentially. This requires very accurate measurements.

Another problem with optical data storage media consists in the fact that the transparent carrier layer made of polycarbonate frequently has internal strains that cause the phenomenon of birefringence. Birefringence also causes scanning errors, since the optical data medium is scanned with the polarized light of a laser.

Furthermore, illuminating the data side of the CD at an acute angle of 45° with a linear polarized light beam is known from DE 44 34 474 A1 of the present applicant. The reflected light beam illuminates a matrix camera. A polarization unit is arranged in front of the matrix camera. With this device it is possible, first of all, to confirm that there is a deformation from the received profile of the light beam on the image plane. Additionally, a conclusion as to a possible birefringence can be drawn from the amount of intensity attenuation. A drawback here consists of the fact that the result of the simultaneously performed detection of birefringence can be influenced by a possible deformation.

The invention is based on the problem of constructing a device and a method of the type described initially such that a very precise detection of a deformation and its extent is possible with simple means. According to another aspect of the invention it should be possible to detect birefringence properties of an optical data medium.

The problem is solved according to the invention in that the light source is constructed as a nearly point-source light emitting uncollimated light and in that imaging optics are provided and adjusted such that the light source is imaged sharply onto the image plane of the photosensitive receiver, so that the surface to be examined acts as a reflective surface, the light source having a known nominal position on the image plane in case of a flawless surface being examined, so that the deformation can be determined from the deviation of the actual position of the image of the light source from the known nominal position of the image of the light source on the image plane. This arrangement has the advantage that, first of all, a simple light source can be employed, which emits uncollimated light. Thus, elaborate diaphragms and optics are avoided.

The prerequisite is merely that these light sources produce a beam lobe with a sufficiently large angle of aperture and uniform illumination intensity. Light-illuminating diodes or SMD light-emitting diode chips, preferably without additional optics, can be employed, for instance, for such a point-source light, of which the generated light spot or light spots have relatively small dimensions, for instance, only a few tenths of a millimeter.

The required aperture angle is dependent on the deviation actually to be measured, that is the largest tilting to be detected. In detail, it is true that the aperture angle must be larger than twice the angle of the maximum tilting to be detected. Thus an aperture angle of 2–20° or merely 4–8° can be sufficient for testing a CD.

Another advantage consists in the fact the only the displacement of an actual position of an image relative to a known and stored nominal position of this image must be determined. Due to the beam profile, it is then possible to draw conclusions indirectly as to the deformation and its extent. An angle measurement is performed with the device according to the invention, so that the error to be measured can be detected indirectly and directly. In this way, the precision is considerably increased.

A special advantage in the employment of light sources that emit uncollimated light is to be seen in the fact that without further effort several light sources can be provided which are imaged jointly onto the image plane of only one single photosensitive receiver. It is thus possible to measure a surface simultaneously at several positions. Since all nominal positions of the images of the individual light sources are known, conclusions as to the profile of the deformation can be drawn from the displacement of one image or another on the matrix image plane.

With the device according to the invention, an exact deformation measurement of a surface can be successfully performed in a simple manner and by simple means. Although the surface to be examined is actually not imaged on the image plane, an unambiguous assignment of the section of the surface to be examined can be achieved.

The imaging optics are as a rule the objective of the camera, which also has the photosensitive receiver with the matrix image plane. The setting of the diaphragm of the objective is crucial to the area of the surface which is covered. If the diaphragm is opened wide, a relatively large surface region is covered, while with a nearly closed diaphragm the area is narrowly limited.

The arrangement of the light sources is in principle arbitrary. It can, for instance, be provided that the light sources are arranged along a straight line. It can also be practical for the light sources to be equally spaced from one another. In this way the profile of a curvature or some other deformation can easily de detected. For an examination of a CD, for instance, it will be turned as rule about an angle of 360°, so that the entire surface can be covered.

In principle, the light sources can also be arranged in a planar configuration, for instance, in the shape of a grid. In this way its is possible to cover even stationary surfaces completely.

It is advantageous as a matter of principle, however, if the light sources are reflected from different radii of the surface to be examined in the case of a round surface to be examined. Here it can be provided for the light sources to be arranged along a radial beam. With only one photosensitive receiver and only one light source arrangement with discrete points of light, it is possible in this way to cover the entire data area of a CD or DVD if the latter is rotated by 360°.

It is fundamentally practical if the light source is arranged as close as possible to the optical axis of the imaging optics of the camera; It is particularly practical with an arrangement of the light sources along a straight line for at least some of the points of light to have an angle of incidence 0–10° onto the surface to be examined of. An angle of incidence of 0° can be brought about by a partially transmissive mirror arranged in the light beam path. These measures have the result that the angle measurement is nearly insensitive with respect to a warp on the surface.

One problem in such a measurement is the unambiguous assignment of the imaged points of light to the light sources generating them. It would be possible in principle for one of the points of light to be imaged by a distortion precisely onto a point of light of another light source and vice versa. The fault could then no longer be precisely detected. It could be practical in this regard if the light sources alternately have different colors. Thus a flawless assignment of the images of the points of light onto the image plane is guaranteed, since the color sequence remains identical in case there is no or only a slight deformation. It can also be provided for at least one light sources to be situated in a defined position with respect to the other light sources, so that an unambiguous assignment of the imaged points of light on the image plane is possible. This can be accomplished, for instance, by marker light sources arranged laterally alongside the light source array.

The displacement of the images on the matrix image plane takes place independently of the type of light used. In particular, other faults or fault phenomena have no influence on these measurements. It is therefore provided, according to an additional embodiment of the invention, to combine the measurement of deformation with a detection of birefringence phenomena. To this end, it is provided that a polarization unit is arranged between at least one light source and the surface to be examined, in order to polarize the emitted light, or alternatively, that at least one light source emits polarized light, and that a corresponding analyzer is provided between the photosensitive receiver and the surface to be examined, in order to be able to detect birefringence properties. The light here can be polarized linearly, elliptically or circularly.

Independently of the type of polarization, one or more light sources are imaged on the image plane. Insofar as a change of intensity takes place, it is possible to infer a fault other than deformation. The change of intensity can then be identified immediately as birefringence. Insofar as a displacement of an imaged point takes place, a deformation can be inferred directly.

Since a linear scanning during rotation of the CD takes place as a rule, alongside the testing of a CD by means of a matrix camera, it is possible to infer the type of flaw precisely from the comparison of the respective images at the identical points. Insofar as the image of the line camera is bright, for instance, while the imaging of the point of light changes there, becoming, for instance, dark or attenuated, a birefringence characteristic must be present at this site. Insofar as both images are dark or attenuated, a different flaw is present, since an attenuation of the image on the line camera cannot be ascribed to birefringence. Completely independent of this, possible deformations are recognized by the displacements of the imaged points of light.

In the method according to the invention for optical detection of the deformation of a surface with a photosensitive receiver having a matrix image plane, the surface is first illuminated by a nearly point-source light emitting uncollimated light. Imaging optics are provided and adjusted such that the light source is sharply imaged on the image plane. The surface to be examined acts here as a reflection surface.

The nominal positions of the images of the light source or sources on the image plane can be determined with a reference surface. In order to be able to obtain a linking of the imaged displacement to the actual deformation, the device can be calibrated with a surface having a defined deformation. For this purpose, for instance, a so-called wobble CD, whose central action is inclined at a defined angle with respect to the axis about which the CD or DVD turns during the testing phase. Subsequently, the deformation can be ascertained from the displacement of the actual position of the image of the light source from the known nominal position of the image of the light source on the picture plane.

It is obvious that the device and the method according to the invention can be implemented with simple means. In particular, very simple light sources can be employed, which need only be shaped in approximately a point form and emit uncollimated light. Independently of the deformation, therefore, at least one of the light beams, and thus the light source, is imaged sharply onto the image plane of the photosensitive receiver. The surface to be examined acts in this case like a mirror, which images the light source in the right position only if the reflecting surface meets the requirements, and is, for instance, flat.

The method and the device are independent of the nature of the surface. It is merely necessary that the surface be at least partially reflective. For a number of surfaces, particularly colored ones, white ones and black ones, but also for transparent surfaces, this is the case. Even reflected light beams of low intensity are sufficient to detect the position of the image, so that information on the deformation of the surface can be obtained.

The invention is described in greater detail below on the basis of the schematic drawing. What is shown are

Figure 1:
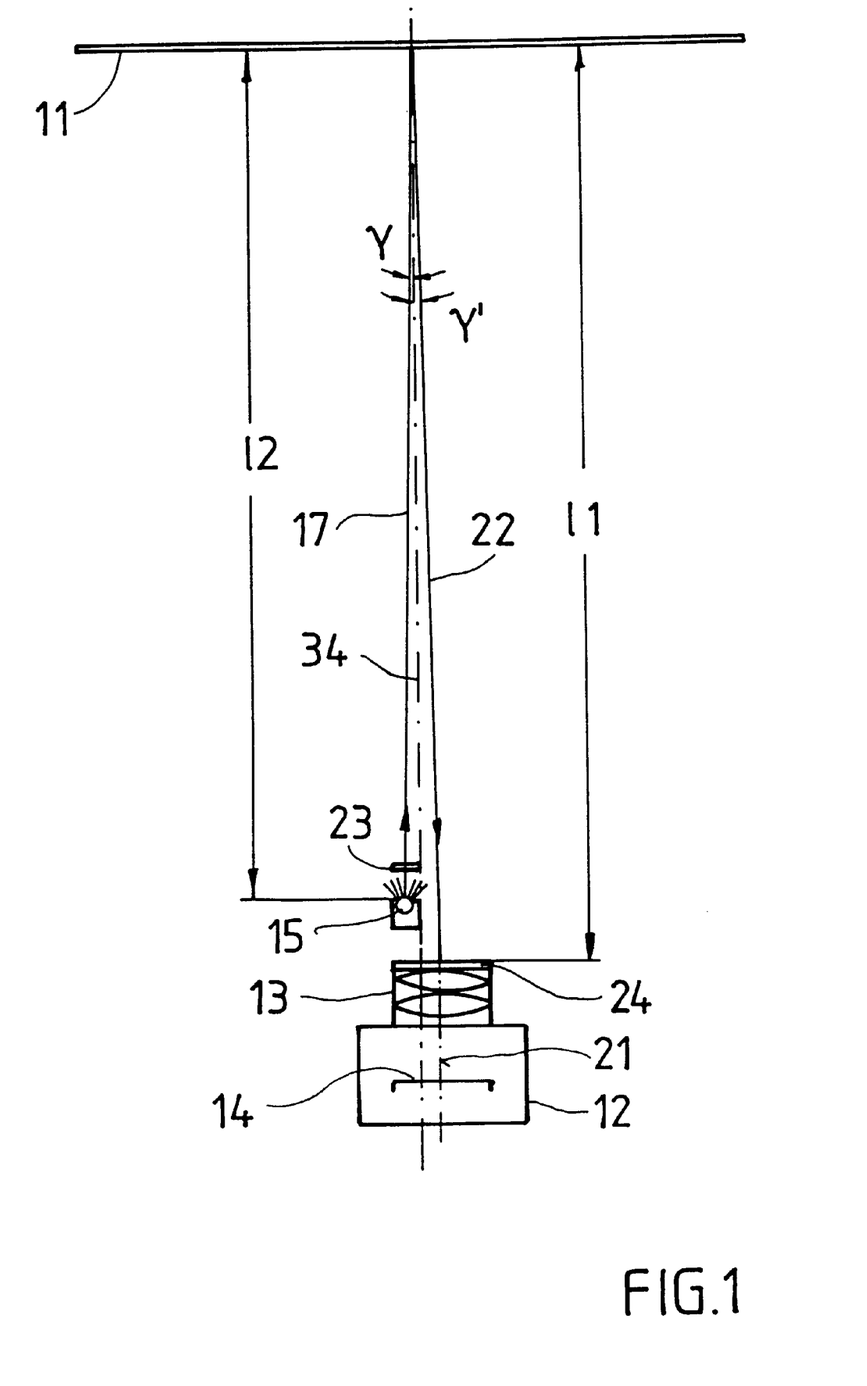
FIG. 1: the fundamental structure of a device according to the invention.

The device for optical detection of a deformation of a surface 11 has a camera 12 with an objective 13 and a photosensitive receiver with a matrix image plane 14. A number of point-source light sources 15, which emit uncollimated light, are provided to expose the photosensitive receiver. The photosensitive receiver is connected by its output to a data-processing system, not shown, in order to be able to evaluated the image generated.

The light sources 15 may be part of an SMD component, on which multiple sufficiently small light-emitting diodes are arranged in a straight line. In principle, it is also possible for the multiple light sources to be produced by a diaphragm, underneath which an illumination means which is large in relation to the dimensions of the holes is arranged. With this, light sources can be produced that have a lobe of rays with a sufficiently large angle of aperture at a uniform illumination intensity. The minimum angle of aperture ω is dependent on the maximum tilting α of the surface to be examined which is to be detected. In principle, the following holds: $\omega \geq 2\alpha$.

The light sources 15 are arrange spaced apart along a straight line 16. Thus a number of discrete illumination points are formed. The imaging optics 13, that is, as a rule, the objective of the camera 12, is adjusted such that the light sources are imaged sharply on the matrix image plane 14 of the photosensitive receiver 12. The surface to be examined 11 acts here as a reflective surface which projects an image of the light sources 15 onto the image plane running essentially parallel to the surface 11. Therefore a line of discrete points of light is likewise produced on the image plane.

As is evident from FIG. 1, the light source 15 radiates light essentially uniformly in all directions. The arrangement is chosen in detail such that at least one light beam 17 is reflected by the surface 11 into the objective 13, so that the light source 15 appears sharp on the image plane 14 as a point of light 18. Preferably, as shown in the drawing, the angle of incidence γ of the beams exposing the photosensitive receiver is chosen such that the light beams strike the surface nearly perpendicularly. This is achieved by placing the light source line 16 as close as possible to the optical axis 34 of the imaging optics 13, as seen from above, without however hindering the incidence of light.

Figure 2:
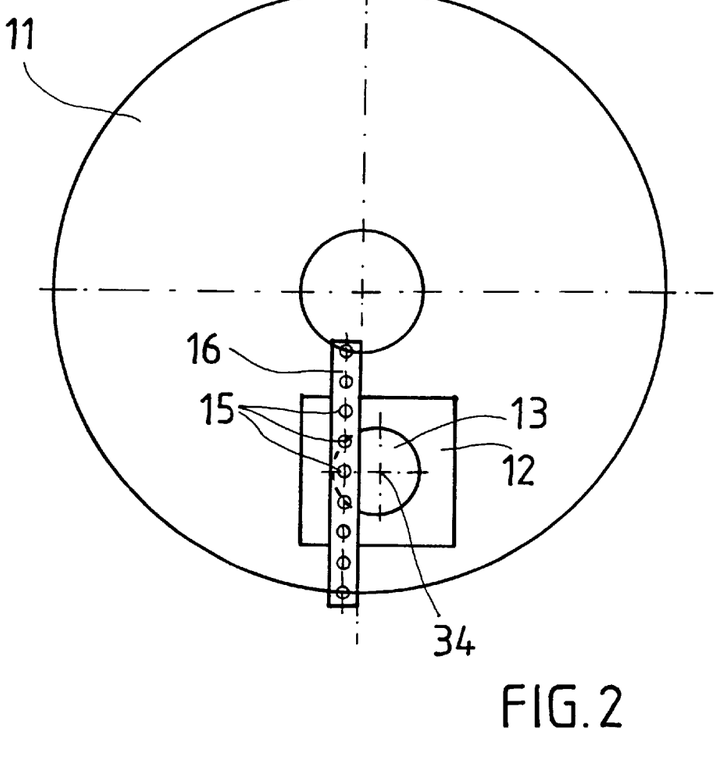
FIG. 2: a plan view of the device according to FIG. 1.

The angle of incidence γ can thus by 0.5–5°, for example 1.5°. This applies, of course, in a spatial arrangement, as is visible, for instance in FIG. 2, only to the light sources that are closest to the optical axis of the objective. For the light sources situated further away the angle of incidence is correspondingly larger.

It is obvious from the beam path that a deformation of the CD, particularly an area inclined with respect to the flat surface, causes a deflection of the light beam in another direction. The angle of reflection γ' relative to the normal position will be larger or smaller depending on the inclination so that the light source will be imaged sharply, but at a deviating position on the image plane 14.

Figure 3:
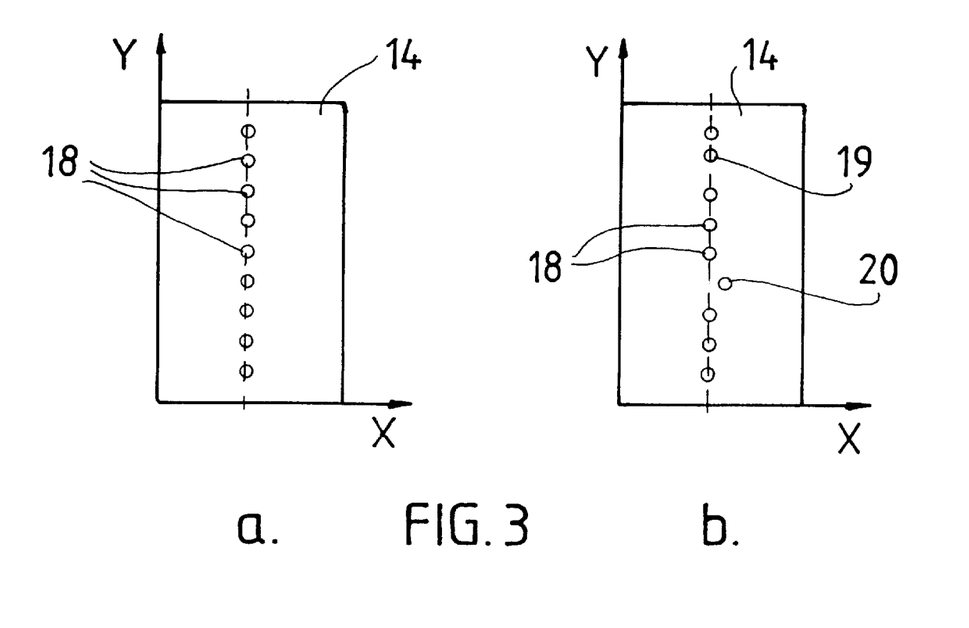
FIGS. 3a–b: the image of the light sources on the matrix image plane of the photosensitive receiver.

This effect is illustrated in FIGS. 3a and 3b. In FIG. 3a, an image of a flat surface without deformations is illustrated. It is obvious that the straight line 16 with the individual light sources 15 is likewise imaged as a straight line of points of light 18. In FIG. 3b, the image of the straight line of light sources after reflection from a surface with deformation is illustrated. The one point of light 19 is displaced by the deformation in the X direction and the other point 20 in the Y direction by the deformation. Naturally, a point of light can also be simultaneously displaced in both directions simultaneously. On the basis of the extent of displacement, the extent of erroneous angular deflection and hence the extent of deformation of the surface can be inferred.

The measured actual position of the points of light 18,19,20 can be determined exactly due to the sharp imaging on the image plane 14. Before the examination, the device need merely be adjusted and calibrated. In the process, the nominal positions of the points of light on the image plane are determined with a flawless surface. Finally a surface with a defined deformation or inclination is examined. In this way, a relation between the measured deviation of the points of light in the X and the Y directions and actual extent of the deformation, that is, an angular error in the radial and/or tangential direction, can be determined.

The advantage of the arrangement is to be seen in the fact that, because of the uncollimated light, the light source can always be imaged sharply and with the same brightness. Therefore, a sharp point of light, whose position can be determined exactly, is always generated on the image plane. Since the angular deviation in the radial and tangential directions is in an unambiguous geometrical relation to the measured deviation in the X and Y directions on the image plane, the actual deformation can be determined exactly.

Another advantage is to be seen in the fact that the light sources 15 can be constructed very simply and occupying very little space. No type of optical elements or diaphragms for concentrating or limiting the light beam are necessary. The light sources 15 can therefore be constructed as LEDs that are arranged along a straight line on an SMD component. It is therefore possible to position the line of lights 16 with the light sources 15 very close to the optical axis 21 of the photosensitive receiver 12. Mirrors or other deflection units are not necessary here. It can even be provided that the line of lights 16 partially covers the objective 13 of the photosensitive receiver. It need only be guaranteed that the light path 22 to the photosensitive receiver is not hindered by the line of lights 16, a light source 15 or some other component of the device. Since the diaphragms can be nearly closed, however, only a small transmission of light to the objective is necessary, so that such obstacles can easily be avoided.

Due to this structure, a very high resolution in the angle measurement can be achieved by simple means. The accuracy depends essentially on the selected distance $l_1$ of the objective and $l_2$ of the light source from the surface 11. The possible resolution per pixel of the image plane results from $$\Delta\alpha/\text{Pixel}[\text{rad}] = 1/(l_2 \times M) \times p$$

M is the imaging scale of the device and results from $$M = L/G = f/(l_1 + l_2)/(1 - f/(l_1 + l_2))$$

p is the pixel size, L the corresponding dimension of the image plane and G the length of the light source line 16. Thus, with $l_1$=220 mm, $l_2$=200 mm and f=25 mm and with an ordinary pixel size of 8 μm, a resolving power of roughly 0.036°/pixel or 0.63 mrad/pixel can be achieved. Since the maximum permissible angular deviation of CDs or DVDs is greater than that by roughly a factor of 10, namely 0.8° radially and 0.3° tangentially, this resolving power is completely sufficient. It is noteworthy in this regard that conventional components can be used, despite the high resolution that can be achieved.

The angle of incidence γ is decisive for the influence of the warp on the measurement. Due to the nearly vertical incidence of the light, the warp has no effect, or only a slight one, on the measurement result.

Since, however, a warp does not arise abruptly, but is instead bounded by at least two angled surface sections, the actual warp can also be ascertained based on the angular deviation ascertained at several points of the radius. The height profile can easily be inferred by integration from the angular deviations. The ascertainment of the warp becomes more exact the more light sources are employed. An integration can be performed easily by means of a data-processing system and is relatively insensitive to outliers among the measured values.

It is obvious that the points of light can be imaged sharply on the image plane, independently of the type of emitted light. Therefore, it is additionally possible to detect other error phenomena with this arrangement, phenomena which have no influence on the position, but only on the intensity of the one or more reflected light beams 22. Thus, for instance, dark sections, scratches and the like can be detected, at least at the illuminated points. In the device shown in FIG. 1, a polarization unit 23 is arranged between the light sources 15 and the surface 11, in order to polarize the emitted light linearly, elliptically or circularly. The polarization unit has the corresponding polarizing filters and delay plates, for instance a λ/4 plate. A corresponding analyzer 24 is arranged in front of the camera 12. In this way, birefringence properties of the surface can be detected.

In detail, the polarization units 23,24 are oriented with respect to one another such that full transmission of light takes place whenever no birefringence occurs on the surface. In that way it is possible for the light sources to be imaged on the image plane in any case. In case of the appearance of a birefringence, the amount of light transmitted by the polarization unit 24 becomes smaller, without any displacement of the point of light taking place, however. Since the effects of the various sources of error are likewise different and cannot influence one another, these two error phenomena can be easily detected with only one photosensitive receiver and with only one generated image.

Since the surface to be examined acts only as a mirror, this has the effect that, in case of a deformation appearing, particularly an inclination of the surface, the actual measuring point 25 to be examined does not coincide with the point on the surface generating the image. This means that a light source 26 associated with a given point 25 of the surface is no longer reflected at this point in case of a deformation. The reflection actually takes place at a point 27 displaced by the value z.

Figure 4:
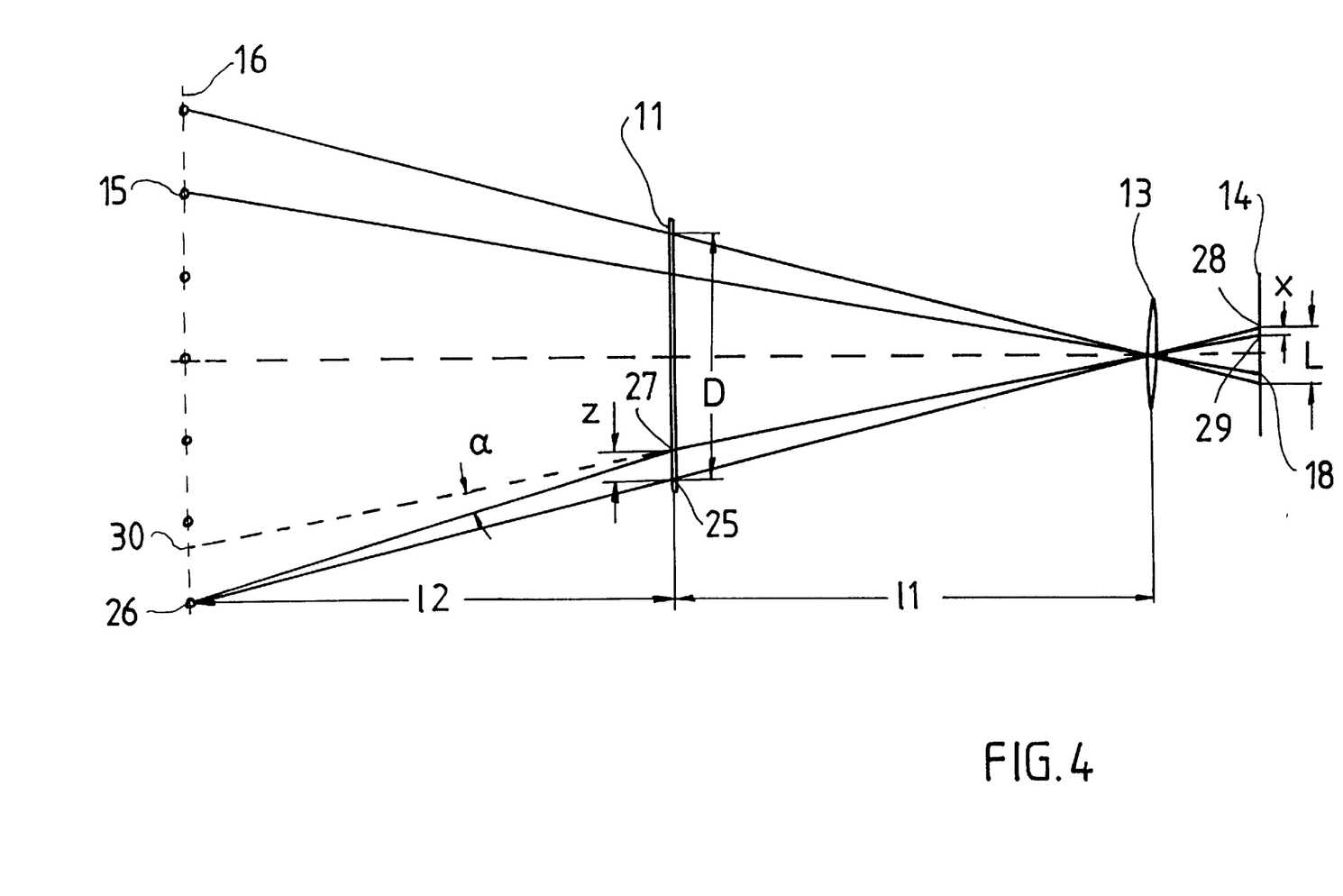
FIG. 4: a diagram to illustrate the imaging relationship.

The actual beam path is shown in a folded-open representation in FIG. 4. The light source 26 is associated with a point 25 of the surface 11 in case of lack of flaws and is projected into the point of light 28 on the image plane 14. Due to an erroneous inclination, however, the light beam is deflected by the angle α, so that the light source is imaged on the point 29 of the image plane 14. This corresponds to a point 30 on the line of lights. The reflection point 27 is correspondingly displaced, so it is not the deformity in point 25 which is being measured. This is a correctable ambiguity, however, which can be eliminated without problems.

In practical terms, such a shift has no effects on the measurement result in any case, since it is not the exact position of the deformation itself that is important in the specific case, but primarily the extent of the deformation. The actual position of the deformation can also be determined precisely. The following holds:

$z=(l_1 \times l_2)/(l_1+l_2) \times \alpha$

The deviation z is correspondingly small and in the above-mentioned embodiment it comes merely to 1.8 mm at an error angle α of 1°.

Figure 5:
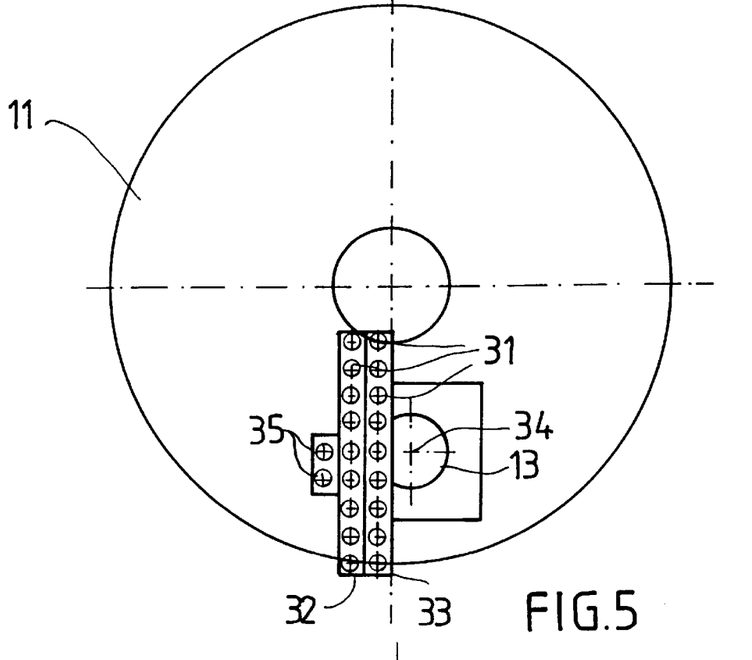
FIG. 5: a plan view of a device according to FIG. 1, but with a different light source arrangement.

For the embodiment illustrated in FIG. 5, the light sources 31 are arranged along two parallel light lines 32,33. Close alongside the light line 33 to the right in the drawing is the optical axis 34 of the camera's objective 13. In detail, the arrangement is made such that only one light line emits polarized light. A possible birefringence can be detected from the change in intensity of the imaged points of light of the one light line. For this purpose, an analyzer, not shown, is provided in front of the camera. The other light line is imaged without loss of intensity on the image plane. With this measure, a better assignment of the individual points of light to the corresponding light sources becomes possible, since in case of the slight tilting usually expected, the two lines are imaged as two parallel series of points of light.

Furthermore, two additional position light sources 35 are provided with this embodiment, which are in a defined relative position to the other light sources 31. In detail, the arrangement is made such that the number of inner and outer light sources is known, so that in case of a disappearance of a point of light on the image plane, for instance, due to scanning an edge area that can no longer reflect back into the objective, it can be determined which light source was no longer imaged. Thus an unambiguous association of imaged point of light and light source can be achieved by simple means.

Figure 6:
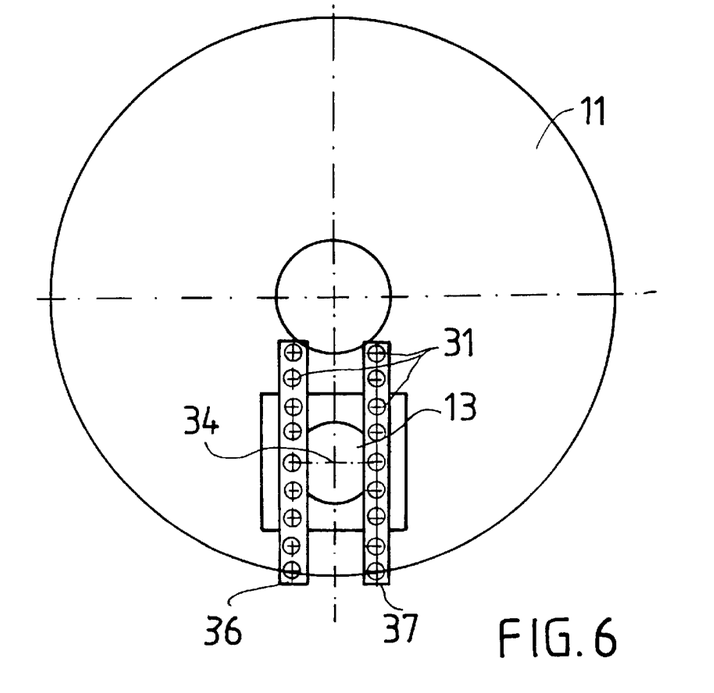
FIG. 6: a plan view of a device according to FIG. 1, but with an additional light source arrangement.
Figure 7:
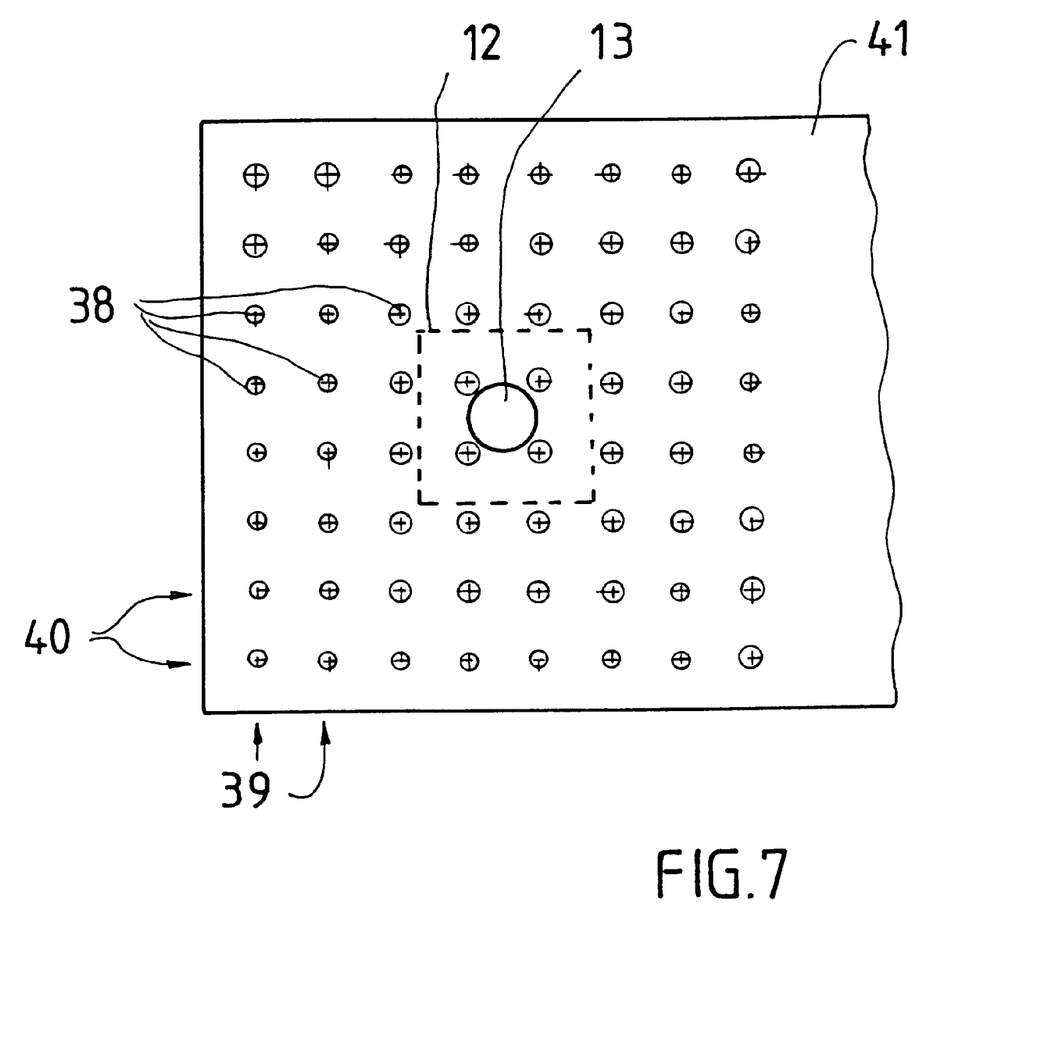
FIG. 7: a plan view onto a device according to FIG. 1, but with yet another light source arrangement.

For the embodiment illustrated in FIG. 6 two parallel lines of light sources 36,37 are likewise provided. One of the lines of light sources is provided with a polarization unit, not shown, in order to emit polarized light. Here the optical axis 34 of the imaging optics 13 is located, however, between the two lines. In FIG. 7, another arrangement of light sources 38 is shown. Here the light sources 38 are arranged in the form of a grid in column direction 39 and row direction 40. The camera 12 is located underneath this arrangement such that the individual reflected light beams strike the photosensitive receiver in the camera or, more precisely, through the diaphragm opening. This arrangement can be advantageous for the testing of stationary or also of linearly moving objects 41, which do not have a round contour. It goes without saying that objects with a round contour can also be covered with this arrangement. For round contours, however, it appears practical to form the light sources in [word omitted from original] along concentric circles, in the center of which the objective of the camera is located.

In principle, it is of course also possible that, for the embodiments shown, only individual light sources 15,31,38 of line of light sources 16,32,33,36,37,39,40 emit polarized light or are provided with a polarization unit.

It is obvious that in this way a device and also a method for the optical detection of a flat, even and smooth surface can be provided with which a high accuracy in the determination of the extent of the deformation can be achieved. Nonetheless, simple, ordinary commercial components can be employed.

The device is suited in particular for the optical testing of a CD or DVD or of some other corresponding optical data medium. In the testing of a CD, the data side is scanned optically by turning the CD at least once about an axis directed perpendicular to the surface. The line with the discrete light sources extends here radially, preferably over the entire data area, that is, roughly half the diameter of the CD or DVD. In this way it is possible to scan the entire surface completely and over several radii simultaneously during one rotation with a line of light sources of the type explained above. The line of light sources additionally extends along a radius, while the optical axis 34 of the imaging optics runs roughly at the height of half the radius.

The device was described above with only one camera. It is of course also possible to employ two or more cameras by way of the appropriated beam splitters. It can be practical in this regard if, for instance, an analyzer is arranged in front of only one camera. In this way the number of possible detectable flaw is increased.

We claim:

1. Device for optical detection of a deformation of a substantially flat surface, comprising:

at least one photosensitive receiver having a matrix image plane which is exposed by at least one light source, the light source is constructed as a nearly point-source light illuminating the substantially flat surface to be examined and emitting uncollimated light; and imaging optics provided in front of the image plane of the photosensitive receiver and adjusted such that the light source is imaged sharply onto the image plane of the photosensitive receiver so that the substantially flat surface to be examined acts as a reflective surface, the light source having a known nominal position on the image plane in case of a flawless substantially flat surface being examined so that the deformation can be determined from a deviation of an actual position of the image of the light source from the known nominal position of the image of the light source on the image plane.

2. Device according to claim 1, wherein several light sources are provided.

3. Device according to claim 2, wherein said light sources are arranged along a straight line.

4. Device according to clam 2, wherein said surface to be examined is disk-shaped, and wherein said light sources are reflected on different radii of said surface.

5. Device according to claim 2, wherein said light sources are arranged two-dimensionally in a grid.

6. Device according to claim 2, wherein said light sources include a line of light-emitting diode chips.

7. Device according to claim 2, wherein said light sources have different alternating colors.

8. Device according to claim 2, wherein one of said light sources is arranged with respect to the other of said light sources such that the image of the light sources on the matrix image plane is unambiguously assigned.

9. Device according to claim 2, wherein at least two lines of light sources are provided, and wherein one of said lines emits polarized light.

10. Device according to claim 2, wherein at least two lines of light sources are provided, and wherein one of said lines is provided with a polarization unit.

11. Device according to claim 2, wherein at least two parallel lines of light sources are provided, and wherein said imaging optics has an optical axis which extends between said two parallel lines of light sources.

12. Device according to claim 1, wherein said at least one light source is arranged close to an optical axis of said imaging optics to provide a steep angle of incidence of the light onto the surface to be examined.

13. Device according to claim 1, wherein said light source has at least one light-emitting diode.

14. Device according to claim 1, wherein said light source has at least one light-emitting diode chip.

15. Device according to claim 1, wherein said light source has a diaphragm with a number of openings under which at least one two-dimensional illumination means is arranged, the dimensions of said illumination means being greater than the dimensions of the openings.

16. Device according to claim 1, further comprising a polarization unit located between said light source and the surface to be examined to polarize the emitted light, and a corresponding analyzer provided between the photosensitive receiver and the surface to be examined so that birefringence properties can be detected.

17. Device according to claim 1, wherein said at least one light source emits polarized light, and further comprising an analyzer provided between the photosensitive receiver and the surface to be examined so that birefringence properties can be detected.

18. Device according to claim 1, wherein the surface to be examined is selected form the group consisting of a CD, a DVD, and an optical data medium.

19. A device according to claim 1, wherein said photosensitive receiver, imaging optics and light source are stationary and said substantially flat surface to be examined is continuously moved relative to said stationary photosensitive receiver, imaging optics and light source during said optical detection.

20. A device according to claim 19, wherein said substantially flat surface is linearly moved relative to said stationary photosensitive receiver, imaging optics and light source.

21. A device according to claim 19, wherein said substantially flat surface is rotated relative to said stationary photosensitive receiver, imaging optics and light source, said rotation is about an axis extending perpendicularly from said substantially flat surface.

22. Method for optical detection of a deformation of a substantially flat surface with at least one photosensitive receiver having a matrix image plane which is exposed by at least one light source, comprising the steps of:

illuminating the substantially flat surface with uncollimated light from at least one nearly point-source light;

adjusting an imaging optical system such that the light source is imaged sharply on the image plane and the substantially flat surface to be examined serves as a reflective surface; and determining the deformation on the basis of a deviation of an actual position of the image of the light source from a nominal position of the image of the light source on the image plane.

23. Method according to claim 22, wherein several light sources are provided which are reflected from various areas of the surface.

24. Method according to claim 23, wherein said light sources are arranged in a straight line.

25. Method according to claim 23, wherein said light sources are arranged in a grid.

26. Method according to claim 22, further comprising the steps of polarizing the light emitted from said light source and passing the light reflected from the surface through an analyzer to detect birefringence.

27. Method according to claim 22, further comprising the steps of emitting polarized light from said light source and passing the light reflected from the surface through an analyzer to detect birefringence.

28. Method according to claim 22, where in the surface to be examined is selected form the group consisting of a data side of a CD, a data side of a DVD, and a data side of an optical data medium.

29. A method according to claim 22, further comprising the step of imparting continuous motion to said substantially flat surface being examined relative to said photosensitive receiver, imaging optics and light source during said optical detection.

30. A method according to claim 29, wherein linear motion is imparted to said substantially flat surface relative to said photosensitive receiver, imaging optics and light source.

31. A method according to claim 29, wherein rotational motion is imparted to said substantially flat surface relative to said photosensitive receiver, imaging optics and light source, said rotational motion is about an axis extending perpendicularly from said substantially flat surface.

32. A device for the optical detection of a deformation of a substantially flat surface, comprising:

at least one photosensitive receiver having a matrix image plane;

at least one point-source light source for emitting uncollimated light onto a moving substantially flat surface being examined such that said light is reflected off of said moving substantially flat surface and exposes said image plane; and imaging optics provided in front of said image plane of said photosensitive receiver and adjusted such that said reflected light is sharply imaged onto said image plane of said photosensitive receiver;

said reflected light having a known nominal position on said image plane relative to an pre-examined flawless substantially flat surface so that the deformation is readily capable of being determined by identification of any deviation of an actual position of the image of the reflected light from said known nominal position of the image of the reflected light on said image plane.

33. A method for the optical detection of a deformation of a substantially flat surface with at least one photosensitive receiver having a matrix image plane which is exposed by at least one light source, comprising the steps of:

imparting continuous motion to a substantially flat surface being examined relative to the photosensitive receiver and the light source;

illuminating, during said motion imparting step, the substantially flat surface with uncollimated light from the light source, said light source being a nearly point-source light source;

adjusting an imaging optical system such that said light reflected off of the moving substantially flat surface is imaged sharply on the image plane; and determining the deformation on the basis of a deviation of an actual position of the image of said light on said image plane relative to a pre-determined nominal position of the image of said light source on said image plane.

* * * * *